United States Patent [19]

Bagchi et al.

[11] Patent Number: 5,665,331
[45] Date of Patent: *Sep. 9, 1997

[54] CO-MICROPRECIPITATION OF NANOPARTICULATE PHARMACEUTICAL AGENTS WITH CRYSTAL GROWTH MODIFIERS

[75] Inventors: Pranab Bagchi, Webster; Raymond P. Scaringe, Rochester, both of N.Y.; H. William Bosch, Bryn Mawr, Pa.

[73] Assignee: NanoSystems L.L.C., Collegeville, Pa.

[*] Notice: The portion of the term of this patent subsequent to Oct. 1, 2013, has been disclaimed.

[21] Appl. No.: 370,998

[22] Filed: Jan. 10, 1995

[51] Int. Cl.$^6$ .............................. A61K 49/04; A61K 9/14
[52] U.S. Cl. .................. 424/9.45; 424/9.4; 424/489; 424/490; 424/488; 424/1.29
[58] Field of Search ........................... 424/9.4, 9.45, 424/450, 9.5, 488, 489, 490

[56] References Cited

U.S. PATENT DOCUMENTS

| | | | |
|---|---|---|---|
| 4,107,288 | 8/1978 | Oppenheim et al. | 424/22 |
| 4,250,113 | 2/1981 | Nordal et al. | 564/153 |
| 4,396,598 | 8/1983 | Lin | 424/5 |
| 4,540,602 | 9/1985 | Motoyama et al. | 427/213.31 |
| 4,713,249 | 12/1987 | Schroder | 424/488 |
| 4,725,442 | 2/1988 | Haynes | 424/490 |
| 4,826,689 | 5/1989 | Violanto et al. | 424/489 |
| 5,118,528 | 6/1992 | Fessi et al. | 427/213.36 |
| 5,145,684 | 9/1992 | Liversidge et al. | 424/489 |
| 5,260,478 | 11/1993 | Bacon et al. | 560/110 |
| 5,264,610 | 11/1993 | Bacon | 560/47 |

OTHER PUBLICATIONS

J. Phys. Chem. 1994, 98, 3215–3221.
J. Am. Chem. Soc. 1985, 107, 311–3122.
Radiology, Jan. 1982, vol. 142, pp. 115–118.
Lachman, et al, "The Theory and Practice of Industrial Pharmacy", Chapter 2, Milling, p. 45, (1986).
Handbook of experimental Pharmacology, pp. 56–73, 1984.
International Journal of Pharmaceutics, 52(1989) 101–108.

Primary Examiner—Gary E. Hollinden
Assistant Examiner—Michael G. Hartley
Attorney, Agent, or Firm—Rudman & Balosh

[57] ABSTRACT

This invention describes the coprecipitation of nanoparticulate pharmaceutical agent dispersion via a process that comprises the dissolution of the said pharmaceutical agent in combination with a crystal growth modifier (CGM) in an alkaline solution and then neutralizing the said solution with an acid in the presence of suitable surface-modifying surface-active agent or agents to form a fine particle dispersion of the said pharmaceutical agent, followed by steps of diafiltration clean-up of the dispersion and then concentration of it to a desired level. This process of dispersion preparation leads to microcrystalline particles of Z-average diameters smaller than 400 nm as measured by photon correlation spectroscopy. Various modification of precipitation schemes are described, many of which are suitable for large-scale manufacture of these agent dispersions. It has been discovered that coprecipitation with CGM leads to smaller particle size compared to a case where precipitation is carried out using the pharmaceutical agent alone. Thus, this dispersion of instant invention is expected to have greater bioavailability. The CGM compound is a compound that has at least about 75% of its chemical structure identical to that of the pharmaceutical agent.

61 Claims, 9 Drawing Sheets

(WITH CRYSTAL
GROWTH MODIFIER)

5 MICRON (WITHOUT CRYSTAL
GROWTH MODIFIER)

5 MICRON

CO-MICROPRECIPITATION OF NANOPARTICULATE PHARMACEUTICAL AGENTS WITH CRYSTAL GROWTH MODIFIERS

FIELD OF THE INVENTION

This invention deals with co-microprecipitation of pharmaceautical agents (diagnostic and therapeutic) with crystal growth modifiers (CGM) as stable, colloidal, nanoparticulate dispersions for pharmaceutical use.

BACKGROUND OF INVENTION

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/mL, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions.. For example, dry milling techniques have been used to reduce particle size and hence influence drug absorption. However, in conventional dry milling, as discussed by Lachman, et al., *The Theory and Practice of Industrial Pharmacy*, Chapter 2, "Milling," p. 45, (1986), the limit of fineness is reached in the region of 100 microns (100,000 nm) when material cakes on the milling chamber. Lachman, et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 µm (1,000–50,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptable large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

U.S. Pat. No. 4,540,602 (Motoyama, et al.) discloses a solid drug pulverized in a aqueous solution of a water-soluble high molecular weight substance using a wet grinding machine. However, Motoyama, et al. teach that as a result of such wet grinding, the drug is formed into finely divided particles ranging from 0.5 µm (500 nm) or less to 5 µm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nanoparticle. A somewhat more involved solvent shift method is described in U.S. Pat. No. 4,826,689 (Violanto) which produces uniform particles of drugs with diameters ranging between 0.5 to 1.0 µm. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmaceutically active material. However, the particles comprise a crosslinked matrix of macromolecules having the active material supported on or incorporated into the-matrix.

U.S. Pat. No. 4,725,442 (Haynes) describes water insoluble drug materials solubilized in an organic liquid and incorporated in microencapsules of phospholipids. However, the toxic effects of solubilizing organic liquids is difficult to overcome. Other methods of formation of pharmaceutical drug microencapsule include:

a) Micronizing a slightly-soluble drug by subjecting a mixture of the drug and a sugar or sugar alcohol to high-speed stirring comminution or impact comminution (EP 411, 629A) together with suitable excipients or diluents. Such a method of encapsule formation does not lead to particle size as small as obtained by milling.

b) Polymerization of a monomer in the presence of the active drug material and a surfactant can lead to small-particle microencapsule (International Journal of Pharmaceutics, Vol. 52, pp. 101–108, 1989). This process, however, contains difficult-to-remove contaminants such as toxic monomers. Complete removal of such monomers can be expensive in manufacturing scales.

c) Co-dispersion of a drug or a pharmaceutical agent in water with droplets of carbohydrate polymer has been disclosed (U.S. Pat. No. 4,713,249 and WO-84/00294). The major disadvantage of the procedure is that in many cases, a solubilizing organic co-solvent is needed for the encapsulation procedure. Removal of traces of such harmful co-solvents can lead to expensive manufacturing processes.

It is noted that filed concurrently herewith are a) EK Docket No. 71869 entitled, "Microprecipitation of Nanoparticulate Pharmaceutical Agents" by Pranab Bagchi et al; b) EK Docket No. 71871 entitled, "Microprecipitation of Nanoparticulate Pharmaceutical Agents Using Surface Active Material Derived from Similar Pharmaceutical Agents" by Pranab Bagchi et al; and c) EK Docket No. 71872 entitled, "Microprecipitation of Micro-Nanoparticulate Pharmaceutical Agents" by Pranab Bagchi et al.

Recently, many successful stable dispersions of nanoparticulate drug or pharmaceutical compositions have been prepared by wet milling of the agent in the presence of surfactants, polymers, block polymers, and oligomers as a mixture thereof as surface modifiers to produce sterically stabilized dispersions of nanoparticulates with particle diameters less than 400 nm (U.S. Pat. No. 5,145,684, WPI 87-200422/29, EP 0,498,482 A2). This wet milling procedure still leads to the incorporation of solubilized heavy metals from the attrition of the milling media, which in many cases must be removed from the dispersion by tedious ion exchange procedures to formulate the final pharmaceutical product.

It would be desirable to provide stable dispersible drug or pharmaceutical agent particles in submicron size range which can be readily prepared which do not appreciably flocculate or agglomerate due to interparticle attraction forces, and do not require the presence of a crosslinked matrix, simultaneously providing enhanced bioavailability of the drug. Furthermore, it would be highly desirable that such formulations do not involve removal of toxic residues such as toxic solvents or heavy metal solubilizates that arise out of attrition of the milling media.

SUMMARY OF THE INVENTION

We have discovered a novel method of preparing stable dispersions of drugs and other pharmaceutical agents in the presence of a surface modifying and colloid stability enhancing surface active agent free of any trace toxic solvents or solubilized heavy metal impurities by the following procedural steps:
1. Dissolving the said pharmaceutical agent along with a crystal growth modifier (CGM) in aqueous base with stirring,
2. Adding above #1 formulation with stirring to a surface active surfactant (or surface modifier) solution to form a clear solution, and,
3. Neutralizing above formulation #2 with stirring with an appropriate acid solution. This procedure can be followed by:
4. Removal of formed salt by dialysis or diafiltration and
5. Concentration of dispersion by conventional means.

The CGM compound is a chemical that has at least 75% of the compound, on a molecule basis, structurally identical to the pharmaceutical agent.

The process of this invention is illustrated in FIG. 1. The process of this invention produces dispersion of pharmaceutical agents with Z-average particle diameter less than 400 nm (as measured by photon correlation spectroscopy) that are stable in particle size upon keeping under room temperature or refrigerated conditions. Such dispersions also demonstrate limited particle size growth upon autoclave-decontamination conditions used for standard blood-pool pharmaceutical agents. Such coprecipitation along with CGM leads to Z-average particle diameters as measured by PCS smaller than in the case where CGM is absent.

There can also be provided a pharmaceutical composition comprising the above-described particles and a pharmaceutically acceptable carrier thereof. Such pharmaceutical composition is useful in a method of treating mammals.

It is an advantageous feature that a wide variety of surface modified drug nanoparticles free of unacceptable contamination can be prepared in accordance with this invention.

Another particularly advantageous feature of this invention is that pharmaceutical compositions are provided exhibiting unexpectedly high bioavailability.

Still another advantageous feature of this invention is that pharmaceutical compositions containing poorly water soluble drug substances are provided which are suitable for intravenous administration techniques.

In other preferred embodiments of this invention, step 3 (FIG. 1) can be carried out in semicontinuous, continuous batch, or continuous methods at constant flow rates of the reacting components in computer-controlled reactors or in tubular reactors where reaction pH can be kept constant using pH-stat systems, as will be described in "Description of Preferred Embodiments." Advantages of such preferred modifications of this invention are clear in that they provide cheaper manufacturing procedures for large-scale production of nanoparticulate dispersion systems.

Another advantage of the invention is that unlike a milled dispersion, the final product is free of heavy metal contaminants arising from the milling media that must be removed due to their toxicity before product is formulated.

A further advantage of the method is that unlike solvent precipitation, the final product of this invention is free of any trace of trace solvents that may be toxic and must be removed by expensive treatments prior to final product formulation.

Another advantage of this invention is that the CGM can enhance the diagnostic or therapeutic characteristic of the final dispersion as it is at least 75% identical to the pharmaceutical agent in question. Structural identity is characterized as having at least 75% of the chemical structure, on a molecular basis, identical to the pharmaceutical agent. The remaining 25% maybe absent or replaced by different chemical structures in the CGM.

DESCRIPTION OF PREFERRED EMBODIMENTS

Figure 1:
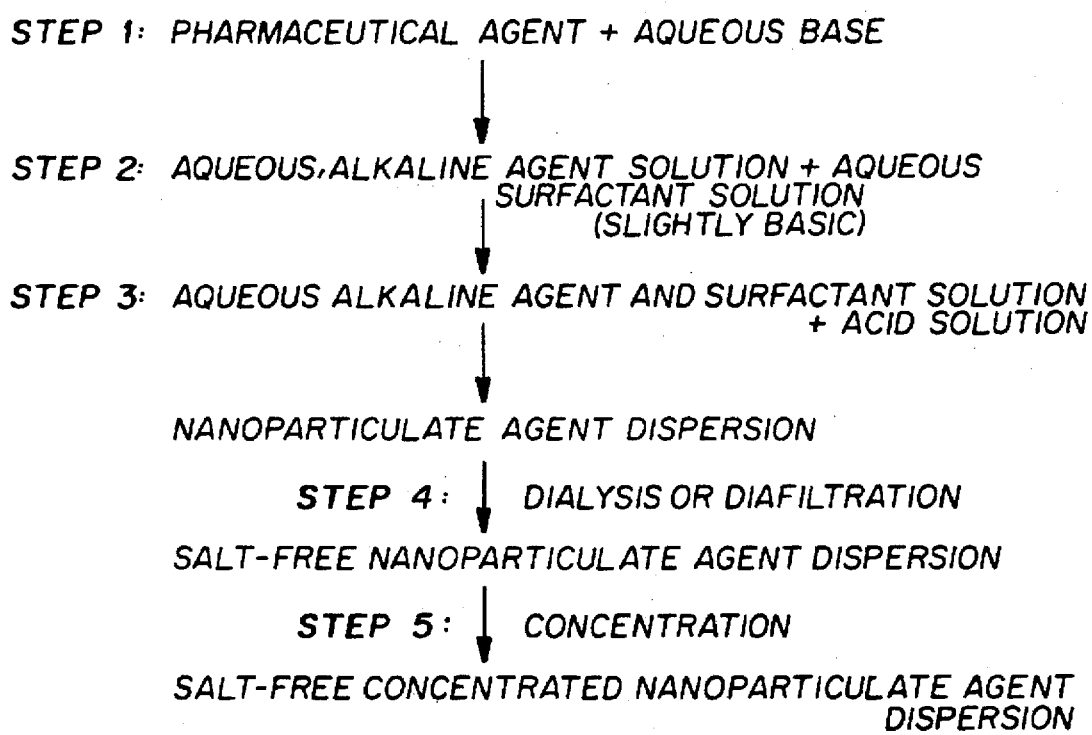
FIG. 1 Schematic for the microprecipitation of nanoparticulate pharmaceutical agents with the crystal growth modifier.

This invention is based partly on the discovery that pharmaceutical agent particles having an extremely small effective average particle size can be prepared by homogeneous nucleation and precipitation in the presence of a surface modifier and a crystal growth modifier (CGM), and that such particles are stable and do not appreciably flocculate or aggregate due to interparticle attractive forces and can be formulated into pharmaceutical compositions exhibiting unexpectedly high bioavailability. While the invention is described herein primarily in connection with its preferred utility, i.e., with respect to nanoparticulate drug substances for use in pharmaceutical compositions, it is also believed to be useful in other applications such as the formulation of particulate cosmetic compositions and the preparation of particulate dispersions for use in image and magnetic recording elements.

The particles of this invention comprise a pharmaceutical agent substance. The said agent substance exists as a discrete, crystalline phase. The crystalline phase differs from a non-crystalline or amorphous phase which results from precipitation techniques, such as described in EPO 275,796 cited above.

The invention can be practiced with a wide variety of pharmaceutical agent substances. The agent substance must be poorly soluble and dispersible in at least one liquid medium. By "poorly soluble" it is meant that the said substance has a solubility in the liquid dispersion medium of less than about 10 mg/mL, and preferably of less than about 1 mg/mL. A preferred liquid dispersion medium is water. However, the invention can be practiced with other liquid media in which a pharmaceutical agent is poorly soluble and dispersible including, for example, aqueous salt solutions, safflower oil, and solvents such as ethanol, t-butanol, hexane, and glycol. The pH of the aqueous dispersion media can be adjusted by techniques known in the art.

Suitable pharmaceutical agents can be selected from a variety of known classes of drugs including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, anti-muscarinic agents, antimycobacterial agents, antineioplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminerigics (antiparkinsonian agents), haemostatics, immuriological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anoretics, sympathomimetics, thyroid agents, vasodilators and xanthines. Preferred drug substances include those intended for oral administration and intravenous administration. A description of these classes of pharmaceutical agents and a listing of species within each class can be found in Martindale, The Extra Pharmacopoeia, Twenty-ninth Edition, The Pharmaceutical Press, London, 1989, the disclosure of which is here by incorporated by reference in its entirety. The drug substances are commercially available and/or can be prepared by techniques known in the art.

The particles of this invention contain a discrete phase of a said substance as described above having a layer of CGM and a surface modifier adsorbed on the surface thereof. Useful surface modifiers are believed to include those which physically adhere to the surface of the drug substance but do not chemically bond to the drug.

Suitable surface modifiers (the term "surface modifiers" is used interchangeably with "surfactants") can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearl alcohol, cetomacrogol emulsifying wax, sorbitan esters, polyoxyethylene alkyl ethers, e.g., ethylene castor oil derivatives, polyoxyethylene sorbitan fatty acid esters, e.g., the commercially available Tweens, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, non-crystalline cellulose, magnesium aluminum silicate, triethanolamine, polyvinyl alcohol, and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986, the disclosure of which is here by incorporated by reference in its entirety. The surface modifiers are commercially available and/or can be prepared by techniques known in the art.

Particularly preferred surface modifiers include polyvinyl pyrrolidone, Pluronic F68 and F108, which are block copolymers of ethylene oxide and propylene oxide, Tetronic 908, which is a tetrafunctional block copolymer derived from sequential addition of ethylene oxide and propylene oxide to ethylenediamine, dextran, lecithin, Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from JCI Specialty Chemicals, and Carbowax 3350 and 934, which are polyethylene glycols available from Union Carbide. Surface modifiers which have found to be particularly useful include polyvinylpyrrolidone, Pluronic F-68, and lecithin.

The surface modifier is adsorbed on the surface of the pharmaceutical agent in an amount sufficient to maintain an effective Z-average particle size of less than about 400 nm as measured by photo correlation spectroscopy. The surface modifier does not chemically react with the drug substance or itself. Furthermore, the individually adsorbed molecules of the surface modifier are essentially free of intermolecular crosslinkages.

In preferred embodiments of the invention, the Z-average particle size is less than about 300 nm. In some embodiments, essentially all of the particles have a size less than 250 nm. When photon correlation spectroscopy (PCS) is used as the method of particle sizing the average particle diameter is the Z-average particle diameter known to those skilled in the art.

Additional surface modifier may be added to the dispersion after precipitation. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of agent substance and surface modifier can vary widely and the optimal amount of the surface modifier can depend, for example, upon the particular drug substance and surface modifier selected, the critical micelle concentration of the surface modifier if it forms micelles, etc. The surface modifier preferably is present in an amount of about 0.1–10 mg per square meter surface area of the drug substance. The surface modifier can be present in an amount of 0.1–90%, preferably 2–60% by weight based on the total weight of the dry particle.

The resulting dispersion of this invention is stable and consists of the liquid dispersion medium and the above-described particles. The dispersion of surface modified drug nanoparticles can be spray-coated onto sugar spheres or onto a pharmaceutical excipient in a fluid-bed spray coater by techniques well-known in the art.

Pharmaceutical compositions according to this invention include the particles described above and a pharmaceutically acceptable carrier therefore. Suitable pharmaceutically acceptable carriers are well-known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment an effective amount of the above-described pharmaceutical composition. The selected dosage level of the agent substance for treatment is effective to obtain a desired therapeutic response for a particular composition and method of administration. The selected dosage level therefore, depends upon the particular drug substance, the desired therapeutic effect, on the route of administration, on the desired duration of treatment and other factors. As noted, it is a particularly advantageous feature that the pharmaceutical compositions of this invention exhibit unexpectedly high bioavailability as illustrated in the examples which follow. Furthermore, it is contemplated that the drug particles of this invention provide more rapid onset of drug action and decreased gastrointestinal irritancy.

It is contemplated that the pharmaceutical compositions of this invention will be particularly useful in oral and parenteral, including intravenous, administration applications. It is expected that poorly water soluble drug substances, which prior to this invention, could not have been administered intravenously, may be administered safely in accordance with this invention. Additionally, drug substances which could not have been administered orally due to poor bioavailability may be effectively administered in accordance with this invention.

While the applicants do not wish to be bound by theoretical mechanisms, it is believed that the surface modifier hinders the flocculation and/or agglomeration of the particles by functioning as a mechanical or steric barrier between the particles, minimizing the close, interparticle approach necessary for agglomeration and flocculation. Alternatively, if the surface modifier has ionic groups, stabilization by electrostatic repulsion may result. It was surprising that stable drug particles of such a small effective average particle size and free of unacceptable contamination could be prepared by the method of this invention.

Representative illustrative species of substances useful in the practice of this invention include the X-ray contrast agent X ethyl-3,5-diacetoamido-2,4,6-triiodobenzoate or X-Ray Contrast Agent "X"

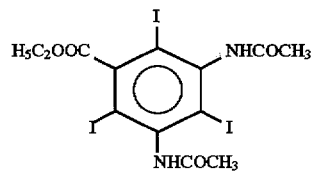

Other illustrative examples of species of pharmaceutical contrast agents include the following compounds.

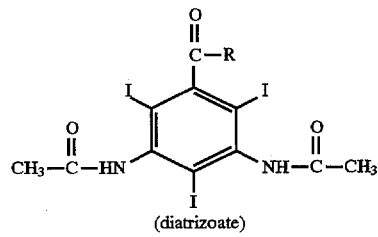

(diatrizoate)

A.

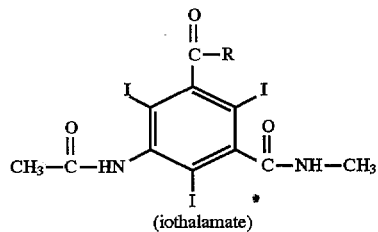

(iothalamate)

B.

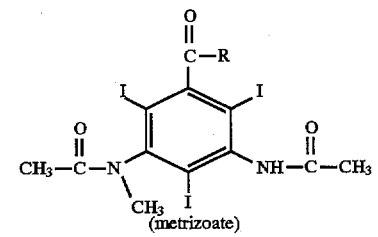

(metrizoate)

C.

and

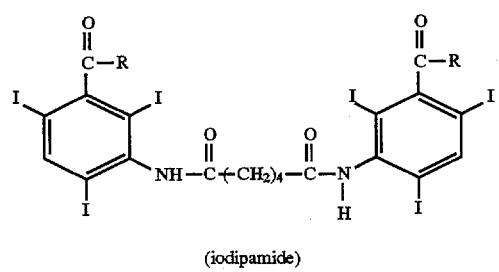

(iodipamide)

D.

In the above structures, R can be OR', OH, or

alkylene

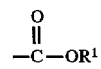

or —O-alkylene

wherein R' is alkyl, and $R^2$ and $R^3$ are independently H or alkyl. Each alkyl group can independently contain from 1–20, preferably 1–8, and more preferably, 1–4 carbon atoms. The alkylene group preferably contains from 1–4 carbons atoms such as methylene, ethylene, propylene and the like, optionally substituted with for example an alkyl group, such as methyl and ethyl.

Particularly preferred contrast agents include the ethyl ester of diatrizonic acid, i.e., ethyl-3,5-diacetamido-2,4,6-triiodobenzoate, also known as ethyl-3,5-bis(acetylamino)-2,4,6-triodobenzoate or tehyl diatrizoate, having the structural formula A above wherein R=—$OCH_2CH_3$ the ethyl glycolate ester of diatrizoic acid, i.e., ethyl(3,5-bis (acetylamino)-2,4,6-triiodobenzoyloxy) acetate, also known as ethyl diatrizoxyacetate, having the structural formula A above wherein

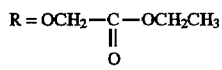

and ethyl-2-(3,5-bis(acetylamino)-2,4,6-triiodobenzoyloxy) butyrate, also known as ethyl-2-diatrizoxybutyrate, having the structural formula A above wherein

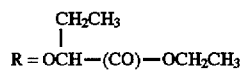

In addition, it is expected that the invention can be practiced in conjunction with the water insoluble iodinated carbonate esters described in PCT/EP90/00053.

The above described X-ray contrast agents are known compounds and/or can be prepared by techniques known in the art. For example, water-insoluble esters and terminal amides of acids such as the above-described iodinated aromatic acids can be prepared by conventional alkylation or amidation techniques known in the art. The above-noted acids and other acids which can be used as starting materials are commercially available and/or can be prepared by techniques known in the art. The examples which follow contain illustrative examples of known synthetic techniques.

The particles useful in the practice of this invention include a surface modifier. Surface modifiers useful herein physically adhere to the surface of the X-ray contrast agent but do not chemically react with the agent or itself. Individually adsorbed molecules of the surface modifier are essentially free of intermolecular cross-linkages.

It is to be noted that agents (therapeutic or diagnostic) that are suitable for this invention must be soluble but remain relatively unhydrolyzed in aqueous alkaline solutions. Compounds described in U.S. Pat. Nos. 5,264,610, 5,260,478 (Bacon) and (application) PRF-469/92 (Bacon, et al.) that are unhydrolyzable in aqueous alkaline solutions are also included herein by reference as agents suitable for the practice of this invention.

The X-ray contrast agent can be an iodinated compound. The iodinated compound can be aromatic or nonaromatic. Aromatic compounds are preferred. The iodinated compound can comprise one, two, three, or more iodine atoms per molecule. Preferred species contain at least two, and more preferably, at least three iodine atoms per molecule. The iodinated compounds selected can contain substituents that do not impart solubility to the compound, such as, for example, alkylureido, alkoxyacylamido, hydroxyacetamido, butyrolactamido, succinimido, trifluoroacetamido, carboxy, carboxamido, hydroxy, alkoxy, acylamino, and the like substituents.

A preferred class of contrast agents includes various esters and amides of iodinated aromatic acids. The esters preferably are alkyl or substituted alkyl esters. The amides can be primary or secondary amides, preferably alkyl or substituted alkyl amides. For example, the contrast agent can be an ester or amide of a substituted triiodobenzoic acid such as an acyl, carbamyl, and/or acylmethyl substituted triiodobenzoic acid. Illustrative representative examples of iodinated aromatic acids include, but are not limited to, diatrizoic acid, metrizoic acid, iothalamic acid, trimesic acid, ioxaglic acid (hexabrix), ioxitalamic acid, tetraiodoterephthalic acid, iodipamide and the like. It is contemplated that poorly soluble derivatives of iodamide and iopyrol can be used herein.

The invention can also be practiced with poorly soluble derivatives, e.g., ester and ether derivatives, of hydroxylated nonionic X-ray contrast agents. Illustrative nonionic contrast agents include, but are not limited to, metrizamide; ioglunide; iopamidol; iopromide; iogulamide; iohexol, and other compounds described in U.S. Pat. No. 4,250,113; ioversol, and other compounds described in U.S. Pat. No. 4,396,598; nonionic triiodinated compounds, such as described in *Investigative Radiology*, Vol. 19, July–August 1984; and nonionic dimers, such as described in Radiology, 142: 115–118, January 1982. The invention can be practiced with poorly soluble derivatives of iodomethane sulfonamides, iodinated aromatic glucoanilides, 2-ketogulonamides, reversed amides, peptides, carbamates, esters, glycoside and glucose derivatives, benzamide derivatives, isophthalamides, his compounds, and bis-polyhydroxylated acylamides, such as described in Volume 73 of the *Handbook of Experimental Pharmacology*, entitled Radiocontrast Agents, edited by M. Sovak, 1984, Springer-Verlag, Berlin, pages 56–73.

Many of the iodinated molecules described above, if in monomeric form, can also be prepared as dimers (sometimes referred to as bis compounds), trimers (sometimes referred to as tris compounds), etc., by techniques known in the art. It contemplated that this invention can be practiced with poorly soluble-iodinated compounds in monomeric, dimeric, trimeric and polymeric forms. Representative illustrative compounds are described by Sovak, cited above, pages 40–53.

A crystal growth modifier is defined, in the context of this invention, as a compound that in the co-precipitation process incorporates into the structure of the microprecipitated crystals of the pharmaceutical agent, there by hindering growth or enlargement of the microcrystalline precipitate, by the so called Ostwald ripening process. A crystal growth modifier (or a CGM) is a chemical that is at least 75% identical in chemical structure to the pharmaceuticl agent. By "identical" is meant that the structures are identical atom for atom and their connectivity. Structural identity is charactarized as having 75% of the chemical structure, on a molecular weight basis, identical to the pharmaceutical agent. The remaining 25% of the structure may be absent or replaced by different chemical structure in the CGM. The pharmaceutical agent may be a therpeutic agent or a diagonostic agent. For example X-ray constants agent "X", described earlier is a diagonostic agent, which we shall use thoughout this present invention as an illustrative example of this instant invention. Therefore, we, in the following provide a list of chemical structures that are suitable as CGM compounds for X-ray contant agent "X".

Crystal Growth Modifier (CGM) "Y" Other CGM's could be compounds with the following structures:

It is noted in the above structures that the CGM compounds are very similar in structure to the X-ray contrast agent "X", and also contain 3 iodine atoms as does the known contrast agent "X". Therfore, in themselves they are also X-ray contrast agents and simultaneously provides this function of X-ray contrast enhancement and also the function of crystal growth modificaion. In other words the CGM compounds used in the method of this invention also provides theraputic or diagonostic efficacy and are not present solely for the purpose of crystal growth modification.

The CMG compound used in the formulation of this invention may vary between 1 to 40% of the weight of the pharmaceutical agent and in a preferred embodiment between 1 to 20% of the weight of the pharmaceutical agent.

Although we do not wish to be limited by this or any theory, we believe that the CMG's of this invention are functioning as "tailor-made" additives. (Z. Berkovitch-Yellin, J. vanMil, L. Addai, M. Idelson, M. Lahav, and L. Leiserowitz, J. Amer. Chem. Soc., 107, 1085, 3111–3122 and B. D. Chen, J. Garside, R. J. Davey, S. J. Maginn, and M. Matsuoka, J. Phys. Chem., 98, 1994, 3215–322). That is say that these molecules are capable of specific interactions with the crystal surface of the phamaceutical agent. This is in contrast to amphiphiles and other surface active agents that are generally belived to function by non-specific interactions with the crystal surface. Tailor-made additives are capable of competing directly with the host molecule for active sites on the growing crystal surface and by virtue of this competition, slow the overall growth rate of the crystal.

METHODS OF THE PERFORMING THE INVENTION

The process of this invention involves a method of preparing stable dispersions of pharmaceutical agents in the presence of a surface modifying and colloid stability-enhancing surface active agent and a crystal growth modifier (CGM) free of trace of any toxic solvents or solubilized heavy metal impurities by the following procedural steps.

1. Dissolving the pharmaceutical agent and the crystal growth modifier in aqueous base with stirring,
2. Adding above #1 formulation, with stirring, to surface active surfactant (or surface modifiers) solution to form a clear solution,
3. Neutralizing above formulation, with stirring, #2 with an appropriate acid solution and optionally,
4. Removal of salts by dyalysis or diafiltration and,
5. Concentration of dispersion by conventional means.

The process of this invention is illustrated in FIG. 1. The process of this invention produces dispersion of photographic agent with Z-average particle diameter, less than 400 nm in diameter, as measured by photon correlation spectroscopy (PCS), that are stable in particle size upon keeping under room temperature or refrigerated conditions. Such dispersions also demonstrate limited particle size growth upon autoclave decontamination conditions used for standard blood-pool pharmaceutical agents.

This invention can also be performed in semicontinuous, continuous, or continuous batch methods. Such methods provide numerous advantages over prior processes of forming dispersions of pharmaceutical agents. The invention provides continuous or semicontinuous methods in which the particle size of the formed dispersions will be reproducible from run to run. Shutdowns of the system can be accomplished with minimum waste or growth of particle size. These and other advantages of the invention will become apparent from the detailed description below.

Figure 2:
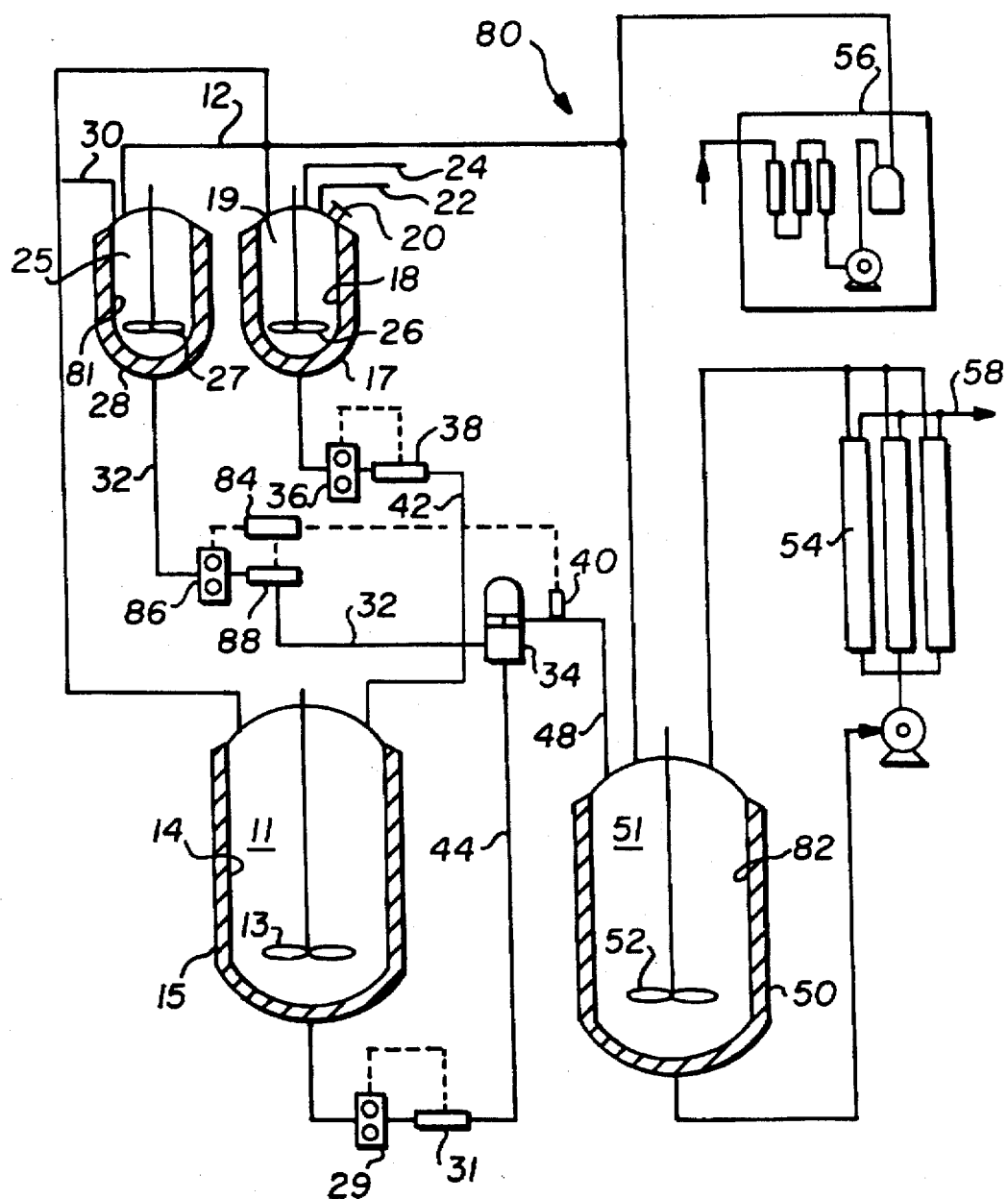
FIG. 2 Schematic for large-scale manufacture of nanoparticulate pharmaceutical agents with CGM.
Figure 3:
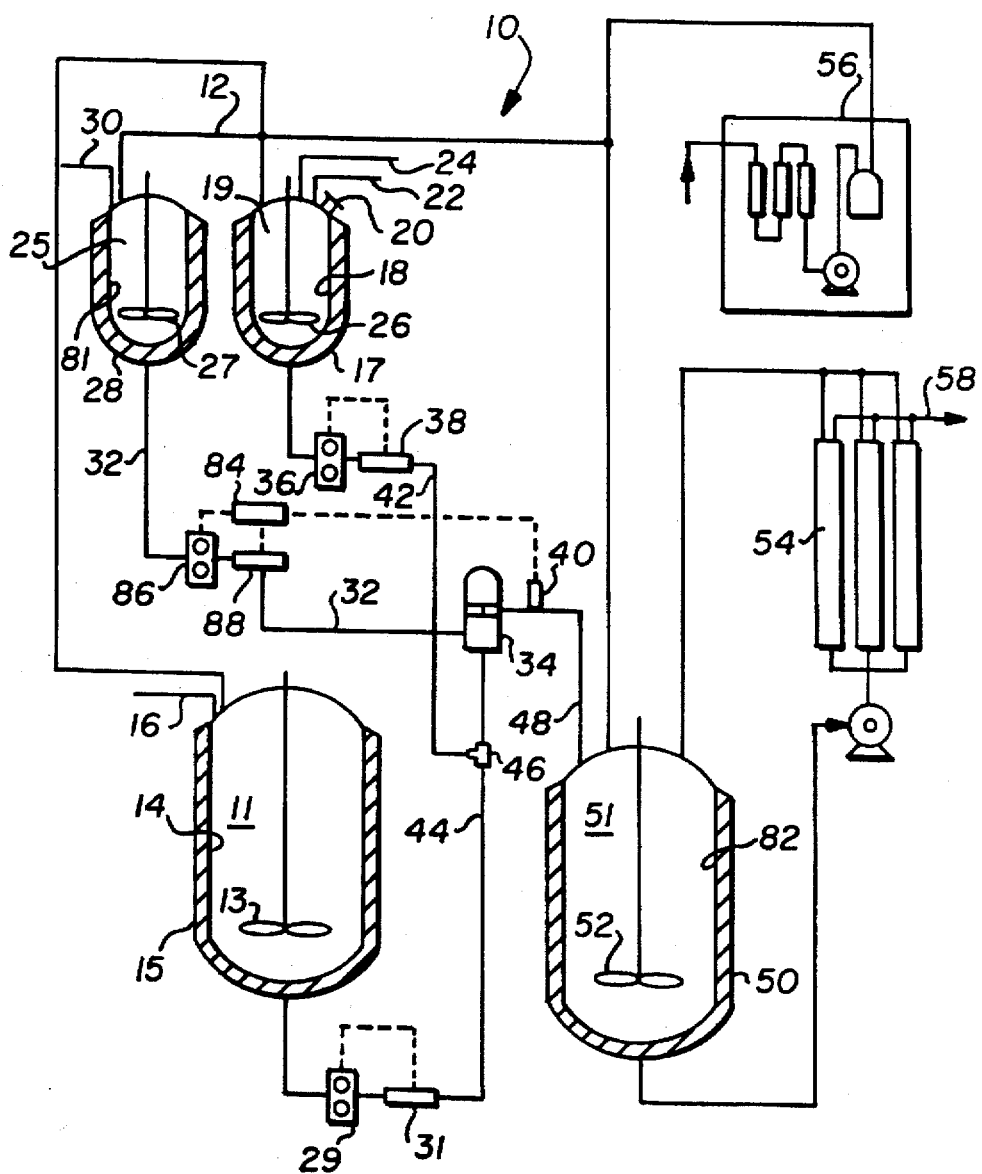
FIG. 3 Schematic for large-scale manufacture of nanoparticulate pharmaceutical agents with CGM using base hydrolyzable surface modifying compounds.
Figure 4:
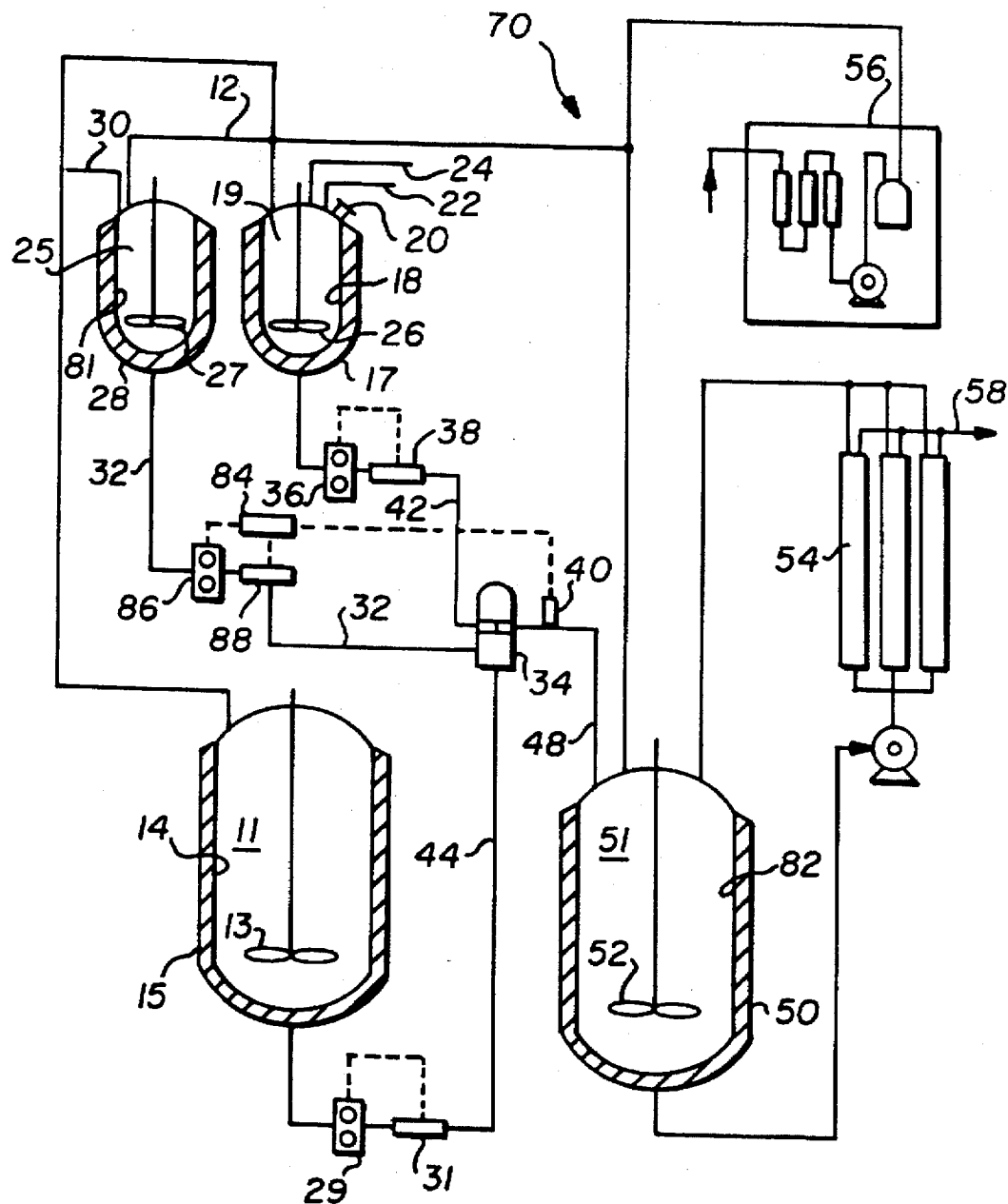
FIG. 4 Schematic for large-scale manufacture of nanoparticulate pharmaceutical agents using base hydrolyzable surfactants by continuous direct mixing.

The schematic of FIG. 2 illustrates apparatus 80 for performing the process of the invention. The apparatus is provided with high purity water delivery lines 12. Tank 14 contains a solution 11 of surfactant and high purity water. Jacket 15 on tank 14 regulates the temperature of the tank. Surfactant enters the tank through line 16. Tank 18 contains a pharmaceutical agent (+CGM) solution 19. Jacket 17 controls the temperature of materials in tank 18. The tank 18 contains a port for delivery of the pharmaceutical agent and the CGM entering through manhole 20, a base material such as aqueous sodium hydroxide solution entering through line 22. The solution is maintained under agitation by the mixer 26. Tank 81 contains acid solution 25 such as propionic acid solution entering through line 30. The tank 81 is provided with a heat jacket 28 to control the temperature, although with the acids normally used, it is not necessary. In operation, the acid solution is fed from tank 81 through line 32 to mixer 34 via the metering pump 86 and flow meter 88. A pH sensor 40 senses the acidity of the dispersion as it leaves mixer 34 and allows the operator to adjust the acid pump 86 to maintain the proper pH in the dispersion exiting the mixer 34. The pharmaceutical agent (+CGM) 19 passes through line 42, metering pump 36, flow meter 38, and joins the surfactant solution in tank 14. In tank 14, the alkaline pharmaceutical agent (+CGM) is mixed with the surfactant solution and is pumped using pump 29 and flow meter 31 into the mixing chamber 34.

The particles are formed in mixer 34 and exit through pipe 48 into the ultrafiltration tank 82. In the preferred process, tank 82, the dispersion 51 is held while it is washed by ultrafiltration membrane 54 to remove the salt from solution and adjust the material to the proper water content for makeup at the proper concentration. The source of high purity water is purifier 56. Agitator 13 agitates the surfactant solution in tank 14. Agitator 27 agitates the acid solution in tank 81. The generated salts are removed during the ultrafiltration process through permeate (filtrate) stream 58.

In some instances, the suitable surface modifier is the surface active agent in an ester that may be base hydrolyzable. An example of such surfactant is Aerosol A102 or Aerosol A103, manufactured by American Cyanamid.

Aerosol A102 ⇒ where m = 10–12, n = 3–5

Aerosol A103 ⇒ 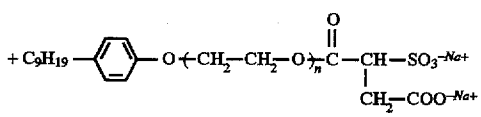 where n = 5–10

During small-scale laboratory precipitation scheme described in FIG. 1, preparation time is short enough such that hydrolysis of the surfactant in alkaline solution is virtually undetectable. However, during manufacturing, mixing and holding time could extend to 1–2 hours. In such case, hydrolysis of the surfactant is substantial and needs to be eliminated by reducing the contact time of the surfactant with the alkali. To accomplish this, the following manufacturing schemes are adopted.

In the following embodiment of the invention, the alkaline pharmaceutical agent with the CGM solution is mixed with the surfactant solution continuously and neutralized within less than a second of mixing in a continuous reactor with acid solution to eliminate surfactant hydrolysis.

The schematic of FIG. 3 illustrates apparatus 10 for performing the process of the invention. The apparatus is provided with high purity water delivery lines 12. Tank 14 contains a solution 11 of surfactant and high purity water. Jacket 15 on tank 14 regulates the temperature of the tank. Surfactant enters the tank through line 16. Tank 18 contains a pharmaceutical agent (+CGM) solution 19. Jacket 17 controls the temperature of materials in tank 18. The tank 18 contains a port for delivery of the pharmaceutical agent (+CGM) entering through manhole 20, a base material such as aqueous sodium hydroxide solution entering through line 22. The solution is maintained under agitation by the mixer 26. Tank 81 contains acid solution 25 such as propionic acid entering through line 30. The tank 81 is provided with a heat jacket 28 to control the temperature, although with the acids normally used, it is not necessary. In operation, the acid is fed from tank 81 through line 32 to mixer 34 via the metering pump 86 and flow meter 88. A pH sensor 40 senses the acidity of the dispersion as it leaves mixer 34 and allows the operator to adjust the acid pump 86 to maintain the proper pH in the dispersion exiting the mixer 34. The pharmaceutical agent (+CGM) 19 passes through line 42, metering pump 36, flow meter 38, and joins the surfactant solution in line 44 at the "T"-fitting 46. The particles are formed in mixer 34 and exit through pipe 48 into the ultrafiltration tank 82. In tank 82, the dispersion 51 is held while it is washed by ultrafiltration membrane 54 to remove the salt from solution and adjust the material to the proper water content for makeup at the proper concentration. The source of high purity water is purifier 56. Agitator 13 agitates the surfactant solution in tank 14. Agitator 27 agitates the acid solution in tank 81. The generated salts are removed during the ultrafiltration process through permeate (filtrate) stream 58.

In some cases, the alkaline pharmaceutical agent (+CGM), the surfactant solution, and the acid solution may be directly and continuously mixed in the continuous mixer to obtain nanoparticulate dispersions. In such a case, the following manufacturing scheme is adopted.

The apparatus 70 schematically illustrated in FIG. 4 is similar to that illustrated in FIG. 3 except that the acid solution in pipe 32, the surfactant solution in pipe 44, and the pharmaceutical agent (+CGM) solution in pipe 42 are directly led to mixing device 34. Corresponding items in FIG. 3 and FIG. 4 have the same numbers. In this system, all mixing takes place in the mixer 34 rather than joining of the surfactant solution and the pharmaceutical agent solution in the "T"-connection immediately prior to the mixer as in the FIG. 3 process.

The previously described methods of this invention find their most preferred use in large-scale production such as in a continuous commercial process. However, preparation of dispersions in pH-controlled conditions can also be practiced on a smaller and/or slower scale in a semicontinuous or continuous manner. The devices of FIGS. 5 and 6 illustrate equipment that is in accordance with the invention for smaller scale production. The device of FIG. 5 was designed for continuous pH-controlled precipitation of dispersions. The apparatus 90 of FIG. 5 provides a continuous means for precipitation of nanoparticulate dispersions. Container 92 is provided with an aqueous surfactant solution 94. Container 96 is provided with an acid solution. Container 100 contains a basic solution 102 of the pharmaceutical agent (+CGM). Container 104 provides a mixing and reacting chamber where the dispersion formation takes place. Container 106 is a collector for the dispersed suspensions 158. In operation, the surfactant solution 94 is metered by pump 108 through line 110 into the reactor vessel 104. At the same time, the basic pharmaceutical agent solution (+CGM) is metered by pump 112 through line 114 into the reactor 104 at a constant predetermined rate. The solutions are agitated by stirrer 116, and acid 98 is metered by pump 118 through line 121 into the reactor 104 to neutralize the solution. The pumping by metering pump 118 is regulated by controller 120. Controller 120 is provided with a pH sensor 122 that senses the pH of the dispersion 124 in reactor 104 and controls the amount and the rate of the addition 0f acid 98 added by pump 118 to neutralize the content of the reaction chamber. The drive for stirrer 116 is 126. The recorder 130 constantly records the pH of the solution to provide a history of the dispersion 124. Metering pump 132 withdraws the dispersion solution from reactor 104 and delivers it to the container 106 using pump 132 and line 150 there it may exit from the outlet 134. In a typical precipitation, there is a basic pharmaceutical (+CGM) agent solution 102, sodium hydroxide solution, and the surfactant. The surfactant is in water, and the neutralizing acid is an aqueous solution of acetic or propionic acid. The reaction chamber has a capacity of about 800 mL. Pharmaceutical agent (+CGM) solution tank 100 has a capacity of about 2500 mL. The surfactant solution tank 92 has a capacity of about 5000 mL. The acid solution tank has a capacity of about 2500 mL, and the dispersion collection tank has a capacity of about 10,000 mL. The temperature is controlled by placing the four containers 92, 96, 104, and 100 in a bath 136 of water 138 whose temperature can be regulated to its temperature up to 100° C. Usually, precipitation is carried out at 25° C. The temperature of the bath 138 is controlled by a steam and cold water mixer (not shown). The temperature probe 140 is to sense the temperature of the reactor. This is necessary for correct pH reading. The neutralization of the basic pharmaceutical agent (+CGM) solution in the reaction chamber 104 by the proportionally controlled pump 118 which pumps in acid solution 98 results in control of pH throughout the run to ±0.2 of the set pH value which is usually about 6.0.

Figure 5:
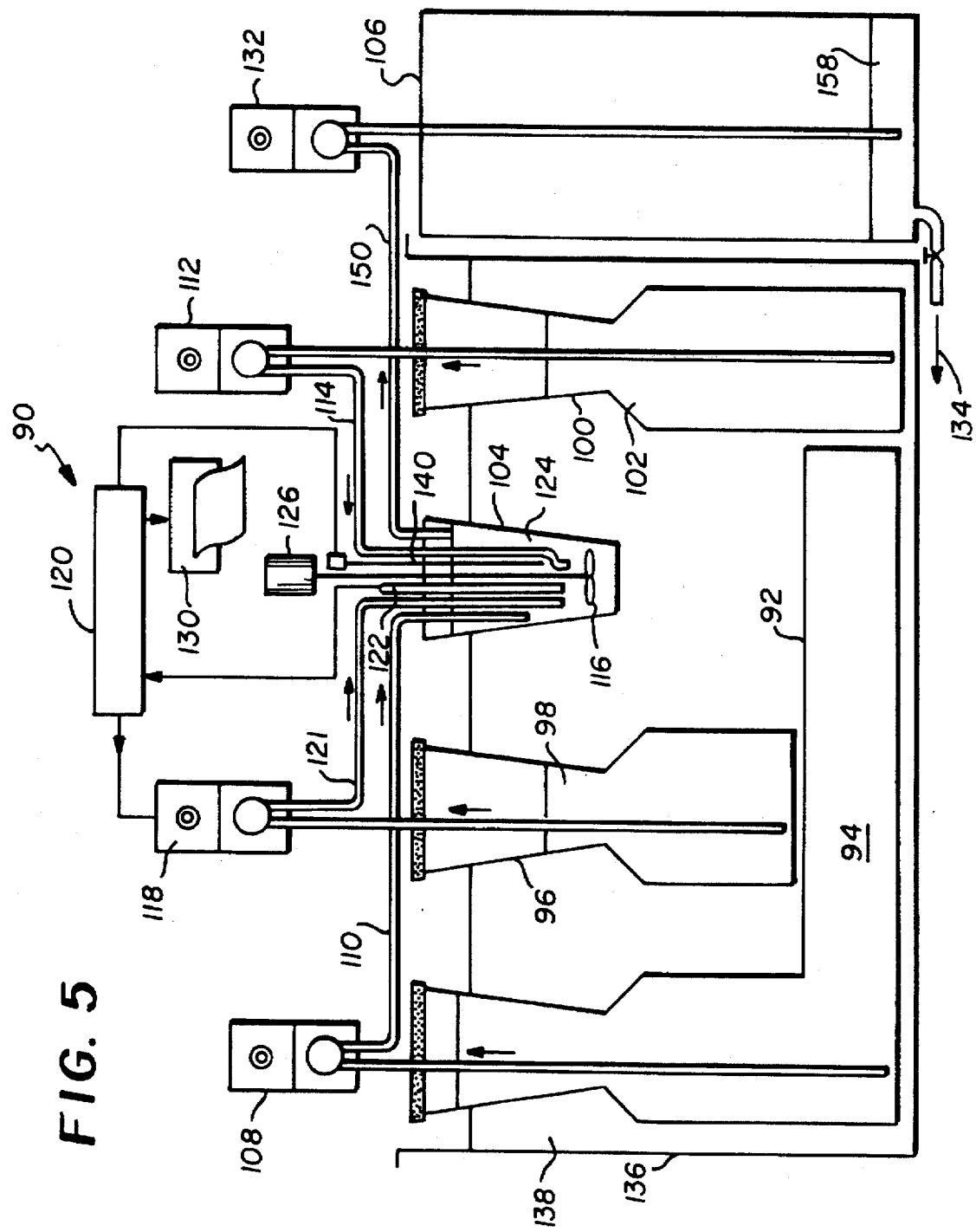
FIG. 5 Schematic for the small-scale pH-controlled microprecipitation device.
Figure 6:
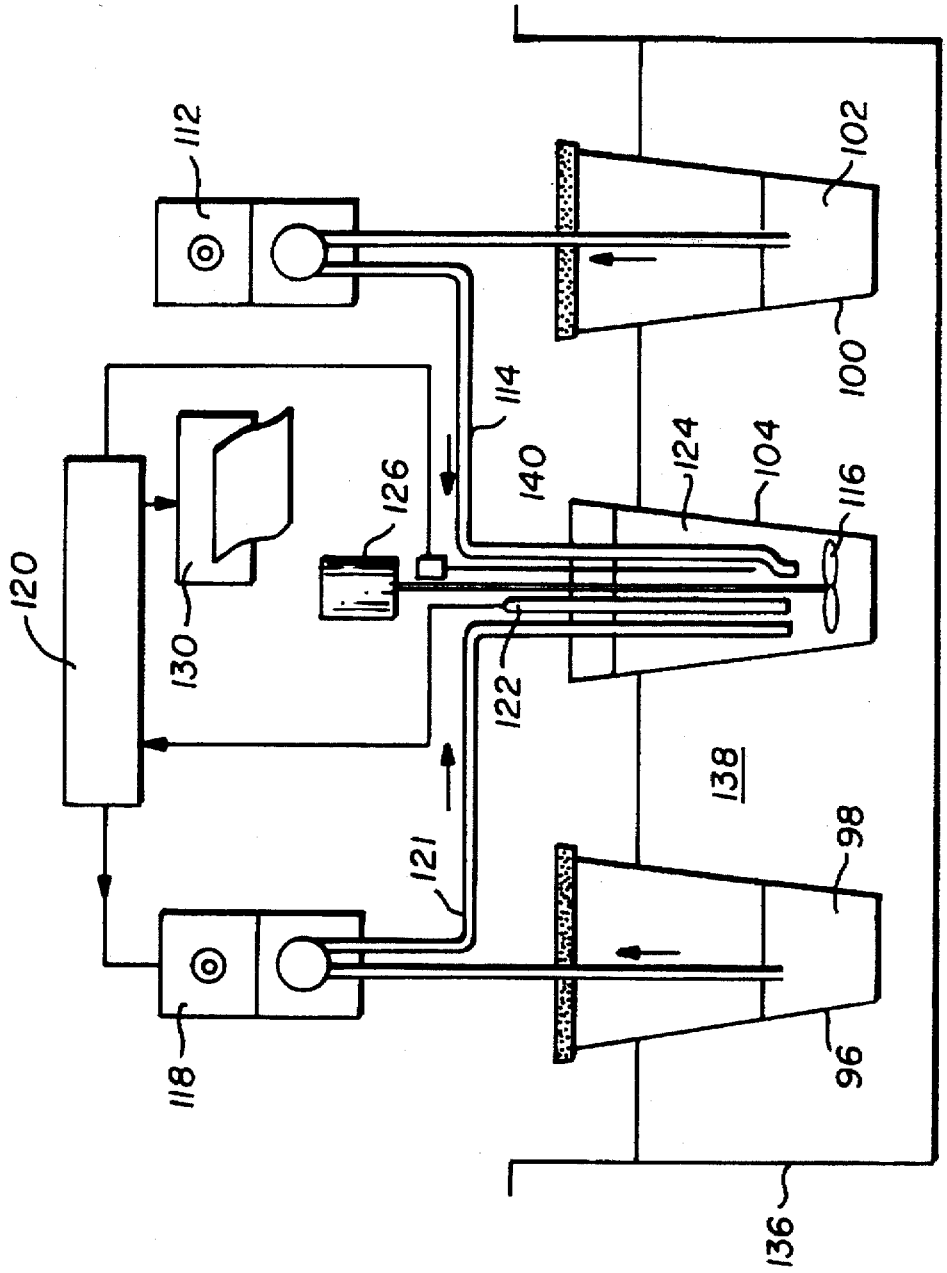
FIG. 6 Schematic for the larger-scale pH-controlled microprecipitation device.

FIG. 6 schematically illustrates a semicontinuous system for forming nanoparticulate dispersions of pharmaceutical materials. Identical items are labeled the same as in FIG. 5. Because of reduced scale, the sizes of acid kettle 96 and the pharmaceutical agent (+CGM) kettle 100 are smaller (about 8100 mL each). In the system of FIG. 6, the reactor 104 is initially provided with an aqueous surfactant solution. In this is pumped a basic solution of photographic agent 102 through pipe 114. 112 is a pH sensor that, working through controller 120, activates pump 118 to neutralize the dispersion to a pH of about 6 by pumping acetic acid 98 through metering pump 118 and line 121 to the reactor 104. Reactor 104 must be removed, dumped, and refilled with the aqueous surfactant solution in order to start a subsequent run.

The base used to solubilize the photographic agent (and CGM) could be any strong alkali as $NH_4OH$, $NaOH$, $KOH$, $LiOH$, $RbOH$, or $CsOH$, or organic bases as amines such as trialkyl amines or pyridine, etc.

The acids used for neutralization in this invention preferably could be any weak acids such as formic, acetic, propionic, butyric acids, etc., or in Some cases, mineral acids such as $HCl$, $H_2SO_4$, $HNO_3$, $HClO_4$, may be preferred.

Other modifications of this invention could be performed according to the processes described in other patents of Bagchi, et al., such as U.S. Pat. Nos. 4,933,270; 4,970,131; 4,900,431; 5,013,640; 5,089,380; 5,091,296; 5,104,776; 5,135,884; 5,158,863; 5,182,189; 5,185,230; 5,264,317; 5,279,931; 5,358,831 and are here by incorporated herein by reference.

Figure 7:
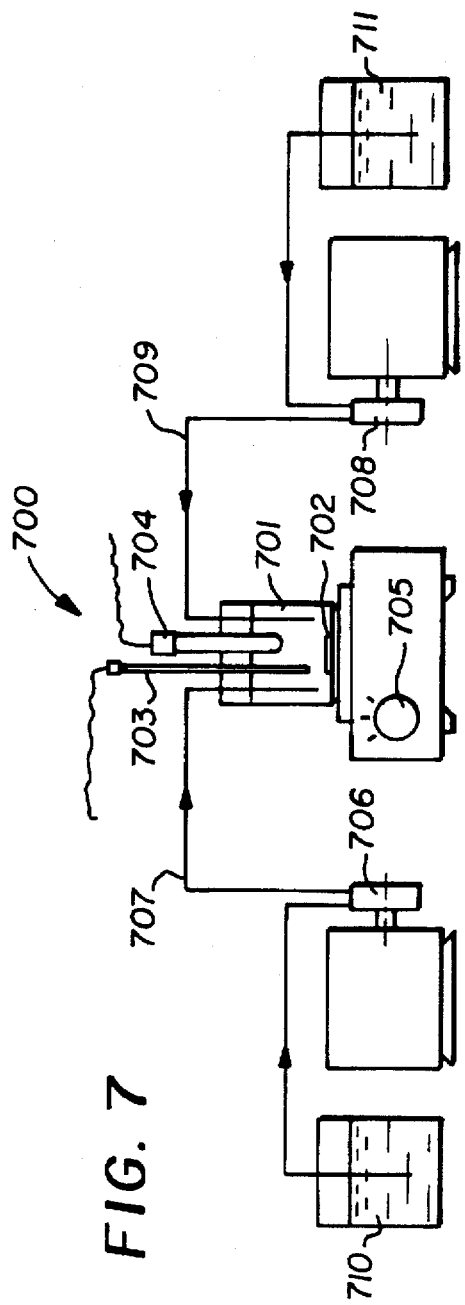
FIG. 7 Schematic for alternate small-scale precipitation of pharmaceutical agents.

Another preferred modification of the precipitation device of this equipment, 700, of this invention is shown in FIG. 7. FIG. 7 schematically depicts a batch system for precipitating crystalline nanoparticulate pharmaceutical agent suspensions. The reactor 701 is initially provided with an aqueous solution of surfactant, or a surface modifier and pH buffer. The reactor is equipped with a magnetic stirring bar 702, a temperature probe 703, and a pH sensor 704. The revolutions of the magnetic stirring bar are maintained at a medium-high level, as controlled by a magnetic plate regulator 705. A strongly basic, particle-free aqueous solution of the pharmaceutical agent (+CGM) is delivered by a pump, 706, with a flow rate control, via tubing 707, to the reactor. Simultaneously, an aqueous acid solution is delivered to the reactor by a pump 708 with a flow rate control via tubing 709. The flow rate of both streams, their concentration, and the duration of their subsurface delivery are carefully selected in such a manner that the final pH is restricted between 3.0 and 7.0, and the final concentration of the suspension is between 0.5% to 10%. Containers 710 and 711 hold the pharmaceutical agent (+CGM) solution and acid solution, respectively.

Figure 8:
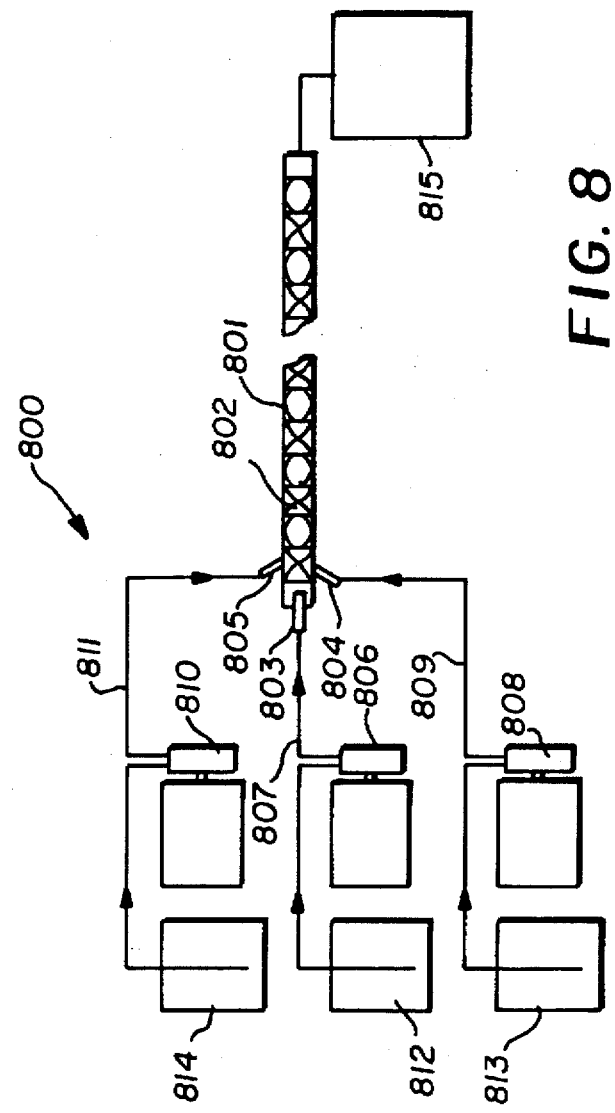
FIG. 8 Schematic of continuous tubular microprecipitation device of this invention.

In another preferred embodiment of the invention continuous precipitation may be carried out in a tubular reactor 800 of FIG. 8.

The neutralization reaction takes place in a tubular reactor, which consists of a tubing or pipe 801 equipped with a static mixer 802. The inlet section of the tubular reactor allows for an influx of three streams through three connectors 803, 804, and 805. Initially, the tubular reactor is supplied with a stream of an aqueous carrier solution of surfactant and pH adjusting buffer, by a pump 806, with a flow rate control, via tubing 807, and the connector 803. A strongly basic, particle-free aqueous solution of the pharmaceutical agent (+CGM) is delivered by a pump 808 with a flow rate control, via tubing 809 and the connector 804, to the tubular reactor. Simultaneously, an aqueous acid solution is delivered to the reactor by a pump with a flow rate control 810, via tubing 811 and the connector 805. The flow rate of the influx streams and their concentration are selected in such a manner that the final pH is less than 7.0, and preferably is between 3.0 and 7.0, and the final concentration of the suspension is between 0.5% to 10%. Containers 812, 813, 814, and 815 hold carrier solution, pharmaceutical agent (+CGM) solution, acid solution, and the product suspension, respectively. The total length of the tubular reactor is such that the reaction is completed before the suspension reaches the outlet of the reactor, at the flow rates of the influx streams and the diameter of the reactor used. In an alternate embodiment of the above apparatus, only two inlet streams are simultaneously delivered to the tubular reactor. The connector 803 is plugged off, and the pump 806 is not shut off. Since the carrier solution is not used, the aggregate volumetric flow rate of the two reactant streams is higher than that typically employed in the three-stream configuration described above.

EXAMPLES

The invention is illustrated in the following examples.

Comparative Example A

Figure 9A:
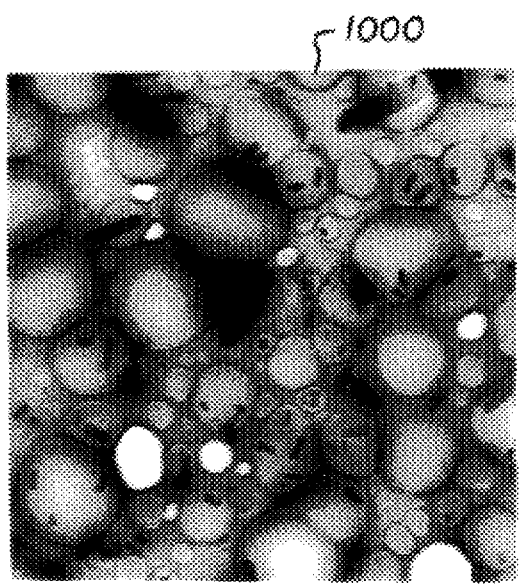
FIG. 9 Cryo-transmission electron photomicrograph of nanoparticulate X-ray contrast agent "X" as prepared by microprecipitation, 1000, without CGM (Comparative Example A) and by microprecipitation by the method of this invention, 2000, with CGM "Y" (Example 1).
Figure 9B:
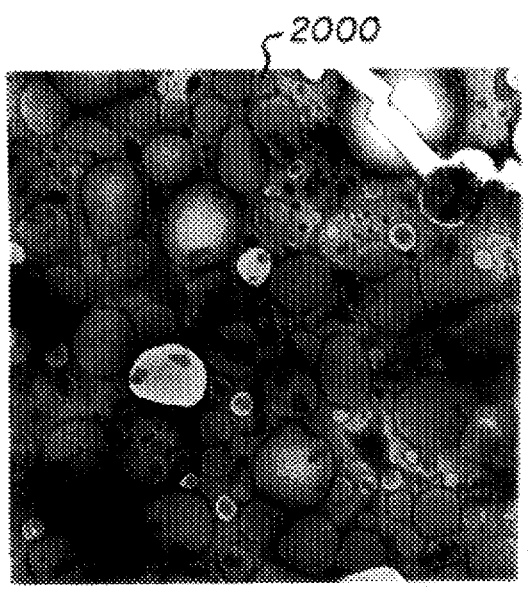

The comparison example of the nanoparticulate X-ray contrast agent "X" was prepared as follows 5 g of the contrast agent "X" was dissolved in 5 g of distilled water and 11.15 g of 20% NaOH solution by heating to 55° C. The solution was then cooled to room temperature. A surface modifying surface active agent solution was prepared by mixing 125 g of distilled water 1.165 g Tetronic T908 and 0.1 g of Aerosol OT. The agent solution was then added to the surfactant solution and the combination was then neutralized with 75 mL of 15% propionic acid. The formed nanoparticulate dispersion of the contrast agent was then washed by dialysis against distilled water for 24 h. The Z-average particle diameter of the formed nanoparticulates dispersion was 274 nm. A cryo-transmission electron photomicrograph of the particles of the dispersion is shown in picture 1000 of FIG. 9. Please note that the semi-circular spots are holes in the polymer film on the microscope grid to hold the dispersion. The nanoparticles of the dispersion are the small crystalline specs.

Example 1

The example of this invention was carried out exactly by the same method as in the comparison example A except 4 g of X-ray contrast agent "X" in combination with 1 g of crystal growth modifier "Y" was used as indicated in the process of this invention according to FIG. 1. After dialysis washing the Z-average particle diameter of the formed nanoparticulate dispersion was determined to be 194 nm. A cryo-transmission photoelectron micrograph of the dispersion is shown in item 2000 of FIG. 9. these results indeed indicate that the use of CGM in the process of this invention leads to smaller dispersion particles than in the case where CGM has not been used. Hence, the dispersion with CGM are expected to have greater bioavailability.

Although we do not wish to be limited by this or any other theory, we believe that the CGM's of this invention are functioning as "tailor-made" additives. (Z. Berkovitch-Yellin, J. vanMil, L. Addai, M. Idelson, M. Lahav, and L. Leiserowitz, J. Amer. Chem. Soc., 107, 1985, 311–3122 and B. D. Chen, J. Garside, R. J. Davey, S. J. Maginn, and M. Matsuoka, J. Phys. Chem., 98, 1994, 3215–322). That is to say that these molecules are capable of specific interactions with the crystal surface of the pharmaceutical agent. This is in contrast to amphiphiles and other surface active agents that are generally believed to function by non-specific interactions with the crystal surface. Tailor-made additives are capable of competing directly with the host molecule for active sites on the growing crystal surface and by virtue of this competition, slow the overall growth rate of the crystal.

Figure 10A:
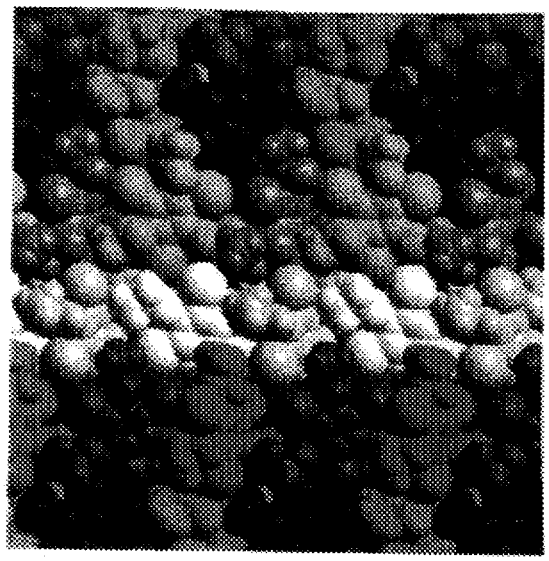
FIG. 10 Crystal surface models of pharmaceutical agent "X" of the invention. (a) Surface model of a crystal surface based on the experimental X-ray structure. (b) Same as (a), but a CGM (compound "Y" of the invention) has been substituted for molecule "X" in the tan surface site only.

As an example of such specific interactions, we explored the ability of CGM "Y" of this invention to compete with pharmaceutical agent "X" on one of the crystal surfaces of "X". FIG. 10a depicts a space-filling model of a native crystal surface of compound "X". The surface structure shown in FIG. 10a is based on the experimentally determined X-ray structure of pharmaceutical agent "X" and the surface depicted is that of the fastest growing crystal face (also experimentally determined). Each molecule in the figure is identical in every detail except for its orientation with respect to the surface. Since the different colored molecules have, by virtue of orientational differences, different groups exposed at the surface, it is also to be expected that their surface binding energies will be different from each other and from molecules in the crystal interior. However, in the interior of the crystal, all molecules will have identical binding energies. Focusing on the tan molecule in FIG. 10a we note that the molecule is, for the most part, buried but has a single amide proton, among other groups, exposed at the surface.

Figure 10B:
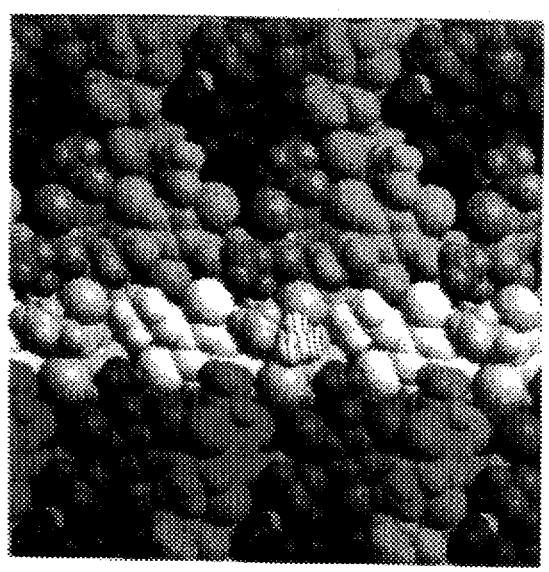

Turning to FIG. 10b, the surface model is identical to that FIG. 10a except that we have replaced one "X" molecule (tan color) with a "Y" molecule for the purpose of illustration. As can be seen in the figure, the added bulk of the extra methyl group (color coded white) does not conflict with the surrounding "X" molecules as there is no interpenetration of this methyl group with any other molecule on the surface. Since the remainder of the molecule is identical to an "X" molecule we arrive at the conclusion that the Y molecule "fits" neatly in to the surface structure of crystal "X".

It turns out that theoretical methods in chemistry have advanced to the point that it is possible to make rather good binding energy estimates for molecules in crystals and crystal surfaces (see for sample, A. K. Rappe and W. A. Goddard III, J. Phys. Chem. 95, 1991, 3358–3363). Such calculations were made for the tan colored molecule X in FIG. 10a and for molecule "Y" in FIG. 10b with the idea that the relative binding energies would provide a measure of molecule Y's ability to compete with molecule "X" for the "tan" binding site. The result is that binding affinity of molecule "Y" is actually 10% stronger than molecule "X" for the "tan" binding sites. Such calculations were repeated for the other seven sites in the surface cell with the result that molecule "Y" could compete with molecule "X" for one of the other binding sites as well.

The basis of the definition of a CGM should now be evident. Only a molecule with substantially the same size, shape, hydrogen bonding capabilities and electronic structure as molecule "X" would likely be able to compete for such stereochemically constrained sites on the surface of "X" crystals. It is this specificity that sets the CGM's of this invention apart from general surface active agents (surface modifiers) and endows them with the ability diminish the growth rate and therefore size of the growing crystalline particles.

The invention has been described in detail with reference to preferred embodiments thereof, but it will be understood that various variations and modifications can be effected within the spirit and scope of the invention.

We claim:

1. A process of forming nanoparticulate dispersions of diagnostic pharmaceutical agents comprising:
   first step of dissolution of the pharmaceutical agent and a crystal growth modifier (CGM) in a aqueous base,
   a second step of adding to it an aqueous solution of one or more surface modifiers and a third step of neutralizing the formed alkaline solution with an acid to form a dispersion,
   wherein the CGM compound is structurally, on a molecular basis, at least 75% identical to the pharmaceutical agent compound.

2. The process of claim 1 wherein the nanoparticulate dispersion is characterized by a Z-average particle diameter less than 400 nm as measured by photon correlation spectroscopy.

3. The process of claim 1 wherein the base is selected from any one or a combination of the following:
   NaOH
   KOH
   CsOH
   trialkyl amines and
   pyridine.

4. The process of claim 1 wherein the neutralizing acid is selected from any one of the following:
   a weak acid and
   a strong acid.

5. The process of claim 1 wherein the neutralizing acid is selected from any one of the following:
   HCl
   $HNO_3$
   $HClO_4$
   $H_2SO_4$
   formic acid
   propionic acid
   acetic acid and
   butyric acid.

6. The process of claim 1 wherein the surface modifier is one or a mixture of:

an anionic surfactant a nonionic surfactant a polymeric molecule and an oligomeric molecule.

7. The process of claim 1 wherein the clean up and concentration of the dispersion is achieved by any one of the methods selected from the following:

diafiltration dialysis and evaporation.

8. The process of claim 1 wherein the nanoparticulate dispersion is characterized by a Z-average particle diameter less than 300 nm a measured by photon correlation spectroscopy.

9. The process of claim 1 wherein the pharmaceutical agent is an X-ray contrast agent.

10. The process of claim 1 wherein the nanoparticulate pharmaceutical agent is concentrated to contain anywhere between 2 to 20% of the agent.

11. The method of claim 1 practiced in any mode selected from the following:

a batch process, a semicontinuous batch process and a continuous process.

12. The method of claim 1 wherein the CGM compound is added in quantity between 1 and 40% of the weight of the pharmaceutical agent.

13. The method of claim 1 wherein the CGM compound is added in quantity between 1 and 20% of the weight of the pharmaceutical agent.

14. The process of claim 1 wherein step 3 is followed by step 4, removal of the formed salts by difiltration or dialysis and step 5, concentrating to desired concentration of the agent dispersion.

15. A process of preparing an aqueous dispersion of a diaganostic pharmaceutical agent comprising:

continuously providing a first solution comprising water and surface modifier or a mixture thereof, continuously providing a second solution comprising a pharmaceutical agent and a crystal growth modifier (CGM) in aqueous base to mix with the first flow, and immediately neutralizing with an acid solution to precipitate nanoparticulate dispersion of said pharmaceutical agent as fine particle colloidal dispersions of said pharmaceutical agent, followed by a salt and solvent removal step by diafiltration or dialysis and then a step of concentrating the dispersion, wherein the CGM compound is structurally, on a molecular basis, at least 75% identical to the pharmaceutical agent compound.

16. The process of claim 15 wherein the nanoparticulate dispersion is characterized by a Z-average particle diameter less than 400 nm as measured by photon correlation spectroscopy.

17. The process of claim 15 wherein the base is selected from any one or a combination of the following:

NaOH

KOH

CsOH trialkyl amines and pyridine.

18. The process of claim 15 wherein the neutralizing acid is selected from any one of the following:

a weak acid and a strong acid.

19. The process of claim 15 wherein the neutralizing acid is selected from any one of the following:

HCl $HNO_3$ $HClO_4$ $H_2SO_4$ formic acid propionic acid acetic acid and butyric acid.

20. The process of claim 15 wherein the surface modifier is one or a mixture of:

an anionic surfactant a nonionic surfactant a polymeric molecule and an oligomeric molecule.

21. The process of claim 15 wherein the clean up and concentration of the dispersion is achieved by any one of the methods selected from the following:

diafiltration dialysis and evaporation.

22. The process of claim 15 wherein the nanoparticulate dispersion is characterized by a Z-average particle diameter less than 300 nm a measured by photon correlation spectroscopy.

23. The process of claim 15 wherein the pharmaceutical agent is an X-ray Contrast agent.

24. The process of claim 15 wherein the nanoparticulate pharmaceutical agent is concentrated to contain anywhere between 2 to 20% of the agent.

25. The method of claim 15 practiced in any mode selected from the following:

a batch process, a semicontinuous batch process and a continuous process.

26. The process of claim 15 wherein the surface modifier is base degradable.

27. The method of claim 15 wherein the CGM compound is added in quantity between 1 and 40% of the weight of the pharmaceutical agent.

28. The method of claim 15 wherein the CMG compound is added in quantity between 1 and 20% of the weight of the pharmaceutical agent.

29. A process of preparing aqueous dispersions of a diagnostic pharmaceutical agent comprising:

continuously providing a first flow of a solution comprising water and surface modifier or a mixture thereof, continuously providing a second flow of a second solution comprising a pharmaceutical agent and a crystal growth modifier (CGM) in aqueous base, continuously providing third flow of a neutralizing acid solution, and mixing the three flows continuously to precipitate a nanoparticulate dispersion of said pharmaceutical agent to form a fine particle dispersion of the said pharmaceutical agent, followed by a salt and solvent removal step by diafiltration or dialysis and then a step of concentrating the said dispersion, wherein the CGM compound is structurally, on a molecular basis, at least 75% identical to the pharmaceutical agent compound.

30. The process of claim 29 wherein the nanoparticulate dispersion is characterized by a Z-average particle diameter less than 400 nm as measured by photon correlation spectroscopy.

31. The process of claim 29 wherein the base is selected from any one or a combination of the following:

NaOH

KOH

CsOH trialkyl amines and pyridine.

32. The process of claim 29 wherein the neutralizing acid is selected from any one of the following:

a weak acid and a strong acid.

33. The process of claim 29 wherein the neutralizing acid is selected from any one of the following:

HCl $HNO_3$ $HClO_4$ $H_2SO_4$ formic acid propionic acid acetic acid and butyric acid.

34. The process of claim 29 wherein the surface modifier is one or a mixture of:

an anionic surfactant a nonionic surfactant a polymeric molecule and an oligomeric molecule.

35. The process of claim 29 wherein the clean up and concentration of the dispersion is achieved by any one of the methods selected from the following:

diafiltration dialysis and evaporation.

36. The process of claim 29 wherein the nanoparticulate dispersion is characterized by a Z-average particle diameter less than 300 nm a measured by photon correlation spectroscopy.

37. The process of claim 29 wherein the pharmaceutical agent is an X-ray contrast agent.

38. The process of claim 29 wherein the nanoparticulate pharmaceutical agent is concentrated to contain anywhere between 2 to 20% of the agent.

39. The method of claim 29 practiced in any mode selected from the following:

a batch process, a semicontinuous batch process and a continuous process.

40. The process of claim 29 wherein the continuous mixing is carried out in any one of the following devices:

a static mixer and a tubular reactor.

41. The process of claim 29 wherein the surface modifier is base degradable.

42. The method of claim 29 wherein the CMG compound is added at a quantity between 1 to 40% of the weight of the pharmaceutical agent.

43. The method of claim 29 wherein the CGM compound is added in a quantity of between 1 and 20% of the weight of the pharmaceutical agent.

44. A process of preparing aqueous dispersions of a diagnostic pharmaceutical agent comprising:

continuously providing a first solution comprising water and surface modifier or a mixture thereof into a solution comprising a pharmaceutical agent and a crystal growth modifier (CGM) in aqueous base to form a first flow, and then neutralizing the first flow with a second flow of an acid solution at a desired pH to form a fine particle dispersion of a pharmaceutical agent, followed by a step of salt and solvent removal by diafiltration or dialysis and then a step of concentrating the said dispersion, wherein the CGM compound is structurally, on a molecular basis, at least 75% identical to the pharmaceutical agent compound.

45. The process of claim 44 wherein the nanoparticulate dispersion is characterized by a Z-average particle diameter less than 400 nm as measured by photon correlation spectroscopy.

46. The process of claim 44 wherein the base is selected from any one or a combination of the following:

NaOH

KOH

CsOH trialkyl amines and pyridine.

47. The process of claim 44 wherein the neutralizing acid is selected from any one of the following:

a weak acid and a strong acid.

48. The process of claim 44 wherein the neutralizing acid is selected from any one of the following:

HCl $HNO_3$ $HClO_4$ $H_2SO_4$ formic acid propionic acid acetic acid and butyric acid.

49. The process of claim 44 wherein the surface modifier is one or a mixture of:

an anionic surfactant a nonionic surfactant a polymeric molecule and an oligomeric molecule.

50. The process of claim 44 wherein the clean up and concentration of the dispersion is achieved by any one of the methods selected from the following:

diafiltration dialysis and evaporation.

51. The process of claim 44 wherein the nanoparticulate dispersion is characterized by a Z-average particle diameter less than 300 nm a measured by photon correlation spectroscopy.

52. The process of claim 44 wherein the pharmaceutical agent is an X-ray contrast agent.

53. The process of claim 44 wherein the nanoparticulate pharmaceutical agent is concentrated to contain anywhere between 2 to 20% of the agent.

54. The method of claim 44 practiced in any mode selected from the following:

a batch process, a semicontinuous batch process and a continuous process.

55. The process of claim 44 wherein the neutralization pH is at any pH value between 3.0 and 7.0.

56. The process of claim 44 wherein the surface modifier is based degradable.

57. A composition comprising a nanoparticulate diagnostic pharmaceutical agent, a crystal growth modifier (CGM), surface modifying surface active agent or agents in water, wherein the CGM compound is structurally, on a molecular basis, at least 75% identical to the pharmaceutical agent compound.

58. The composition of claim 57 wherein the surface modifier is one or a mixture of an anionic surfactant a nonionic surfactant a polymeric molecule and an oligomeric molecule.

59. The composition of claim 57 wherein the nanoparticulate pharmaceutical agent dispersion has a Z-average particle size 3 nm than 400 nm, as determined by Photon Correlation Spectroscopy (PCS).

60. The composition of claim 57 wherein the nanoparticulate pharmaceutical dispersion has a Z-average particle size less than 250 nm, as determined by PCS.

61. An x-ray contrast agent comprising the composition of claim 57.

* * * * *